United States Patent
Kline (10) Patent No.: US 7,998,084 B2
(45) Date of Patent: Aug. 16, 2011

(54) METHOD AND SYSTEM FOR DIAGNOSING POST-SURGICAL PULMONARY VASCULAR OCCLUSIONS

(75) Inventor: Jeffrey A Kline, Charlotte, NC (US)

(73) Assignee: Charlotte-Mecklenburg Hospital Authority, Charolette, NC (US)

( * ) Notice: Subject to any disclaimer, the term of this patent is extended or adjusted under 35 U.S.C. 154(b) by 950 days.

(21) Appl. No.: 11/556,738

(22) Filed: Nov. 6, 2006

(65) Prior Publication Data

US 2007/0078357 A1    Apr. 5, 2007

Related U.S. Application Data (60) Continuation-in-part of application No. 11/160,960, filed on Jul. 18, 2005, now Pat. No. 7,066,892, which is a division of application No. 10/400,339, filed on Mar. 26, 2003, now Pat. No. 7,083,574, which is a division of application No. 09/965,303, filed on Sep. 27, 2001, now Pat. No. 6,575,918.

(51) Int. Cl.
A61B 5/08    (2006.01)

(52) U.S. Cl. .............. 600/532; 600/529

(58) Field of Classification Search ............ 600/532
See application file for complete search history.

(56) References Cited

U.S. PATENT DOCUMENTS

| | | | | |
|---|---|---|---|---|
| 5,533,512 A | * | 7/1996 | Novotny et al. | 600/532 |
| 6,629,933 B1 | * | 10/2003 | Lindner | 600/532 |
| 2007/0129646 A1 | * | 6/2007 | Heinonen et al. | 600/532 |
| 2007/0185405 A1 | * | 8/2007 | Altobelli et al. | 600/529 |

* cited by examiner

*Primary Examiner* — Patricia C Mallari
(74) *Attorney, Agent, or Firm* — George R. McGuire; Bond Schoeneck & King (57) ABSTRACT

A method of determining the presence of pulmonary embolism is a postoperative patient using the carbox ratio of the patient prior to the surgical procedure and the carbox ratio of the patient after to the surgical procedure. The characteristics of the breath of the patient are obtained prior to a surgical procedure for a baseline and then afterwards if the patient has difficult breathing. The mean carbox ratios from the baseline and post-surgical data collections are then compared to non-invasively predict the likelihood that the patient has developed pulmonary embolism. A decrease in the carbox ratio of more than twenty-five percent (25%) represents an abnormal test and is consistent with possible pulmonary embolism. No change or an increase in the carbox ratio suggests the absence of pulmonary embolism.

20 Claims, 5 Drawing Sheets

METHOD AND SYSTEM FOR DIAGNOSING POST-SURGICAL PULMONARY VASCULAR OCCLUSIONS

CROSS-REFERENCE TO RELATED APPLICATIONS

This application is a continuation-in-part of U.S. patent application Ser. No. 11/160,960, filed on Jul. 18, 2005, which is a divisional of U.S. patent application Ser. No. 10/400,339, filed on Mar. 26, 2003, which is a divisional of U.S. patent application Ser. No. 09/965,303, filed on Jun. 10, 2003.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. R42 HL086316-01 awarded by the National Institutes of Health.

BACKGROUND OF THE INVENTION

1. Field of the Invention

The present invention relates to vascular occlusions of the respiratory system, and more particularly to a non-invasive method for the diagnosis of pulmonary embolism and related disorders.

2. Description of the Related Art

A pulmonary embolism occurs when an embolus becomes lodged in lung arteries, thus blocking blood flow to lung tissue. An embolus is usually a blood clot, known as a thrombus, but may also comprise fat, amniotic fluid, bone marrow, tumor fragments, or even air bubbles that block a blood vessel. Unless treated promptly, a pulmonary embolism can be fatal. In the United States alone, around 600,000 cases occur annually, 10 percent of which result in death.

The detection of a pulmonary embolism is extremely difficult because signs and symptoms can easily be attributed to other conditions and symptoms may vary depending on the severity of the occurrence. Frequently, a pulmonary embolism is confused with a heart attack, pneumonia, hyperventilation, congestive heart failure or a panic attack. In other cases, there may be no symptoms at all.

Often, a physician must first eliminate the possibility of other lung diseases before determining that the symptoms, if any, are caused by a pulmonary embolism. Traditional diagnostic methods of testing involve blood tests, chest X-rays, and electrocardiograms. These methods are typically more effective in ruling out other possible reasons than for actually diagnosing a pulmonary embolism. For example, a chest x-ray may reveal subtle changes in the blood vessel patterns after an embolism and signs of pulmonary infarction. However, chest x-rays often show normal lungs even when an embolism is present, and even when the x-rays show abnormalities they rarely confirm a pulmonary embolism. Similarly, an electrocardiogram may show abnormalities, but it is only useful in establishing the possibility of a pulmonary embolism.

As a pulmonary embolism alters the ability of the lungs to oxygenate the blood and to remove carbon dioxide from the blood, one method of diagnosing the condition involves taking a specimen of arterial blood and measuring the partial pressure of oxygen and carbon dioxide in the arterial blood (i.e., an arterial blood gas analysis). Although a pulmonary embolism usually causes abnormalities in these measurements, there is no individual finding or combination of findings from the arterial blood gas analysis that allows either a reliable way to exclude or specific way of diagnosing pulmonary embolism. In particular, at least 15-20% of patients with a documented pulmonary embolism have normal oxygen and carbon dioxide contents of the arterial blood. Accordingly, the arterial blood analysis cannot reliably include or exclude the diagnosis of a pulmonary embolism.

The blood D-dimer assay is another diagnostic method that has become available for commercial use. The D-dimer protein fragment is formed when fibrin is cleaved by plasmin and therefore produced naturally whenever clots form in the body. As a result, the D-dimer assay is extremely sensitive for the presence of a pulmonary embolism but is very nonspecific. In other words, if the D-dimer assay is normal, the clinician has a reasonably high degree of certainty that no pulmonary embolism is present. However, many studies have shown a D-dimer assay is only normal in less than ⅓ of patients and thus produces a high degree of false positives. As a result, the D-dimer assay does not obviate formal pulmonary vascular imaging in most patients with symptoms of a pulmonary embolism.

In an attempt to increase the accuracy of diagnostic, physicians have recently turned to methods which can produce an image of a potentially afflicted lung. One such method is a nuclear perfusion study which involves the injection of a small amount of radioactive particles into a vein. The radioactive particles then travel to the lungs where they highlight the perfusion of blood in the lung based upon whether they can penetrate a given area of the lung. While normal results can indicate that a patient lacks a pulmonary embolism, an abnormal scan does not necessarily mean that a pulmonary embolism is present. Nuclear perfusion is often performed in conjunction with a lung ventilation scan to optimize results.

During a lung ventilation scan, the patient inhales a gaseous radioactive material. The radioactive material becomes distributed throughout the lung's small air sacs, known as alveoli, and can be imaged. By comparing this scan to the blood supply depicted in the perfusion scan, a physician may be able to determine whether the person has a pulmonary embolism based upon areas that show normal ventilation but lack sufficient perfusion. Nevertheless, a perfusion scan does not always provide clear evidence that a pulmonary embolism is the cause of the problem as it often yields indeterminate results in as many as 70% of patients.

Pulmonary angiograms are popular means of diagnosing a pulmonary embolism, but the procedure poses some risks and is more uncomfortable than other tests. During a pulmonary angiogram, a catheter is threaded into the pulmonary artery so that iodine dye can be injected into the bloodstream. The dye flows into the regions of the lung and is imaged using x-ray technology, which would indicate a pulmonary embolism as a blockage of flow in an artery. Pulmonary angiograms are more useful in diagnosing a pulmonary embolism than some of the other traditional methods, but often present health risks and can be expensive. Although frequently recommended by experts, few physicians and patients are willing to undergo such an invasive procedure.

Spiral volumetric computed tomography is another diagnostic tool that has recently been proposed as a less invasive test which can deliver more accurate results. The procedure's reported sensitivity has varied widely, however, and it may only be useful for diagnosing an embolism in central pulmonary arteries as it is relatively insensitive to clots in more remote regions of the lungs.

These pulmonary vascular imaging tests have several disadvantages in common. Nearly all require ionizing radiation and invasiveness of, at a minimum, an intravenous catheter. The imaging tests also typically involve costs of more than $1,000 for the patient, take more than two hours to perform, and require special expertise such as a trained technician to perform the tests and acquire the images and a board-certified radiologist to interpret the images. Notably, none are completely safe for patients who are pregnant. As a result of these shortcomings, the imaging procedures are not available in many outpatient clinic settings and in many portions of third world countries.

With respect to postoperative care, the disadvantages of CT angiography include need for patient transport, 60-180 min to perform and interpret the scan, need for special equipment and technician availability, need for radiologist availability to interpret, significant renal toxicity from contrast, risk of allergy, significant dose of radiation and increased lifetime risk of death from cancer, and $2000 charge. The ventilation-perfusion lung scan suffers from limited availability, time to perform, need for special expertise to perform and interpret, and a very low rate of findings that definitively exclude or diagnose pulmonary embolism in the post-surgical population. The blood test known as the D-dimer can also be used to rule out pulmonary embolism in ambulatory patients, but surgery causes the D-dimer to increase in a very unpredictable way. Hence, the D-dimer suffers from very low diagnostic specificity in the post-surgical population.

BRIEF SUMMARY OF THE INVENTION

It is therefore a principal object and advantage of the present invention to provide a method for non-invasively diagnosing postoperative pulmonary vascular occlusions that does not require specialized technicians.

It is an additional object and advantage of the present invention to provide a method for non-invasively diagnosing postoperative pulmonary vascular occlusions that is not expensive.

It is a further object and advantage of the present invention to provide a method for non-invasively diagnosing postoperative pulmonary vascular occlusions that is easy to use.

It is another object and advantage of the present invention to provide a method for non-invasively diagnosing postoperative pulmonary vascular occlusions that is accurate.

In accordance with the foregoing objects and advantages, the present invention comprises a method of determining the presence of pulmonary embolism is a postoperative patient. The first step is the preoperative collection of data obtained from the breath of the patient. The patient is allowed to breathe the ambient air for two minutes, and is then seated in a semi-Fowler's position and given with comfortable nose clips. The patient is next provided with and asked to breath through the device of the present invention. The data obtained by the device is qualified against predetermined criteria and, if acceptable, stored in memory. After an operation, the collection process is repeated if the patient experiences difficulty breathing. The mean carbox ratios from the baseline and post-surgical data collections are then compared to non-invasively predict the likelihood that the patient has developed pulmonary embolism. For example, a decrease in the carbox ratio of more than twenty-five percent (25%) represents an abnormal test and is consistent with possible pulmonary embolism. No change or an increase in the carbox ratio suggests the absence of pulmonary embolism.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 1:
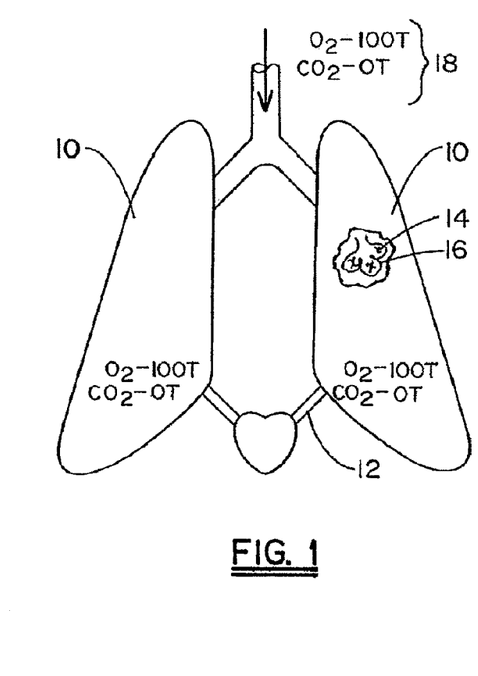
FIG. 1 is an illustration of a respiratory system during inhalation.

Referring now to the drawing in which like reference numerals refer to like parts throughout, there is seen in FIG. 1 a representation of lungs 10 free from any pulmonary occlusions. In healthy lungs 10, blood flows freely from the pulmonary arteries 12 into the capillaries 14 surrounding the individual alveoli 16 of the lungs 10. When inhaled air 18 is drawn into the lungs 10 and alveoli 16, oxygen is transferred from the inhaled air 18 to the blood stream and carbon dioxide is transferred out. Inhaled air 18 typically contains an oxygen partial pressure of approximately one hundred (100) torr and a carbon dioxide partial pressure of zero (0) torr.

Figure 2:
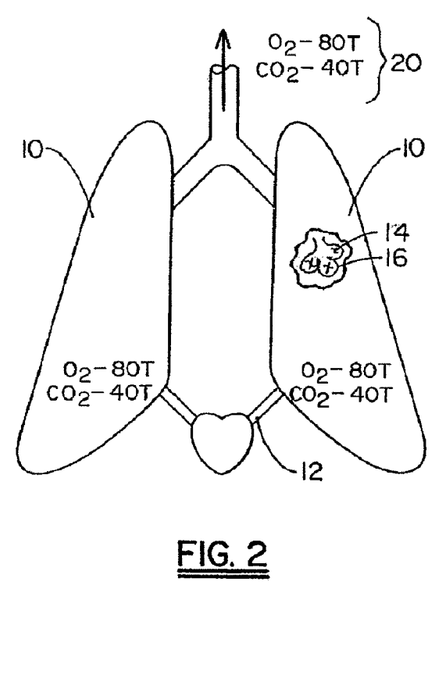
FIG. 2 is an illustration of a respiratory system during exhalation.

Once the inhaled air 18 reaches the alveoli 16, the oxygen content decreases while the carbon dioxide content increases until an equilibrium with blood gas levels in the pulmonary arteries 12 is reached. The inhaled air 18 is then, as seen in FIG. 2, expired as exhaled air 20. Exhaled air 20 from properly functioning lungs typically contains a partial pressure of oxygen of about eighty (80) torr and a partial pressure of carbon dioxide of about forty (40) torr.

Figure 3:
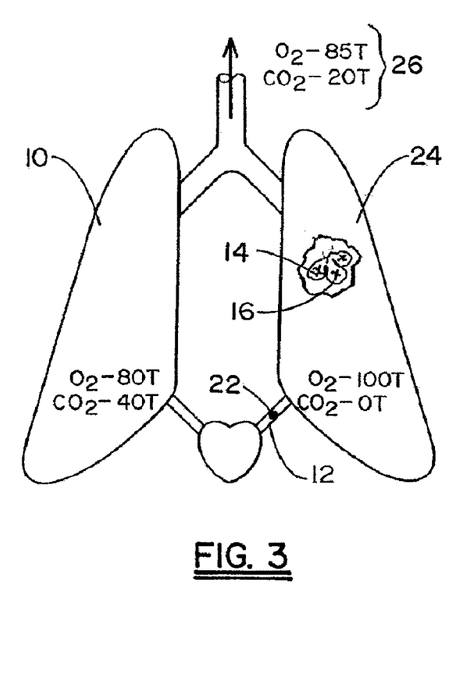
FIG. 3 is an illustration of a respiratory system afflicted with a pulmonary vascular occlusion during exhalation.

FIG. 3 depicts the functioning of a respiratory system afflicted with a pulmonary embolism 22 which, as an example, occludes blood flow to an afflicted lung 24. As a result, there is a reduction in the number of alveoli 16 that participate in gas exchange. This volume of space available in the alveoli 16 that is lost from participation is commonly referred to as alveolar deadspace. Due to the deadspace and loss of total alveolar volume available for gas exchange, afflicted lung 24 does not exchange gases as readily as the healthy lung 10. Accordingly, exhaled air 26 contains a higher partial pressure of oxygen and lower partial pressure of carbon dioxide than air exhaled from a healthy lung. In the example depicted in FIG. 3, exhaled air 26 exiting the respiratory system contains a partial pressure of oxygen of about eighty-five (85) torr and a partial pressure of carbon dioxide of about twenty (20) torr. Thus, the ratio of carbon dioxide to oxygen in exhaled air 26 from afflicted lung 24 (i.e., 20:85) is smaller than the ratio in exhaled air 20 from healthy lung 10 (i.e., 40:80) as seen in FIG. 2.

Figure 4:
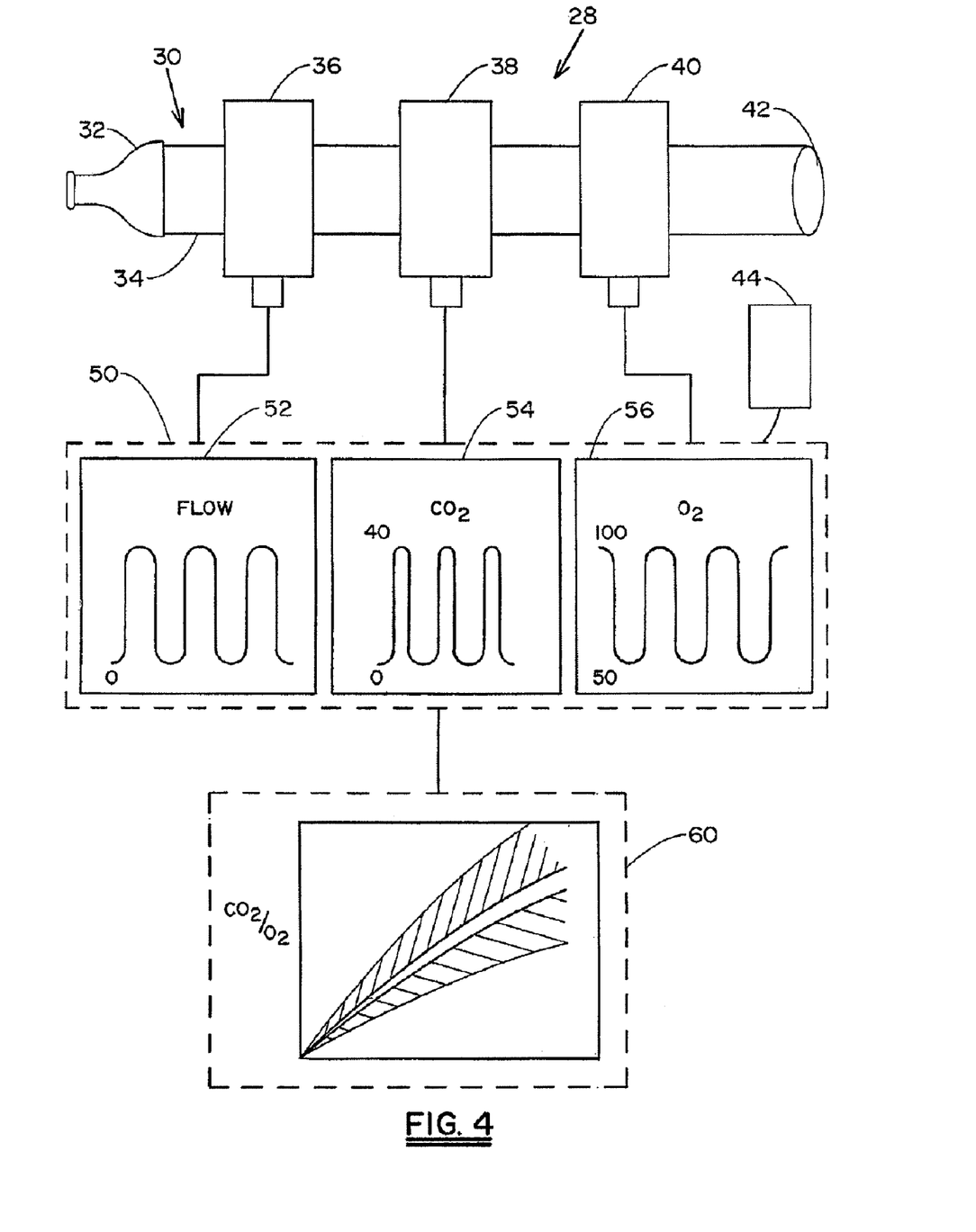
FIG. 4 is a schematic representation of the system of the present invention.

As seen in FIG. 4, a system 28 for measuring and diagnosing pulmonary disorders comprises a measuring unit 30 in combination with a data processing unit 50 and a display screen 60. Measuring unit 30 determines the overall flow of air inhaled into and exhaled out of the lungs while simultaneously determining the partial pressure of oxygen and carbon dioxide. Data processing unit 50 computes the concentrations of carbon dioxide, oxygen, and nitrogen from the partial pressures and determines the ratio of carbon dioxide to oxygen from the raw data obtained by measuring unit 30. The ratio of carbon dioxide to oxygen is then plotted against expired volume on display screen 60. By comparing the carbon dioxide ratios to average readings, the likelihood that a given patient has a pulmonary embolism can be determined.

Measuring unit 30 comprises a patient mouthpiece 32 connected in fluid communication to a breathing tube 34 having an open end 42 through which air can be inhaled or exhaled. Measuring unit 30 further comprises three sensors; a pneumotach 36, a capnometer 38, and an oxygen monitor 40. The three sensors are situated in series and in-line with breathing tube 34 for simultaneously measuring the flow, carbon dioxide, and oxygen levels of inhaled and exhaled air. Infrared and paramagnetic type sensors are preferred respectively. Sensors using spectrometric techniques may also work for both oxygen and carbon dioxide measurements providing they can supply data with rapid enough response time for breath-to-breath, real-time plotting. The mainstream technique for measuring the inhaled or exhaled air is preferred, but the sidestream technique may also be effective.

Figure 5:
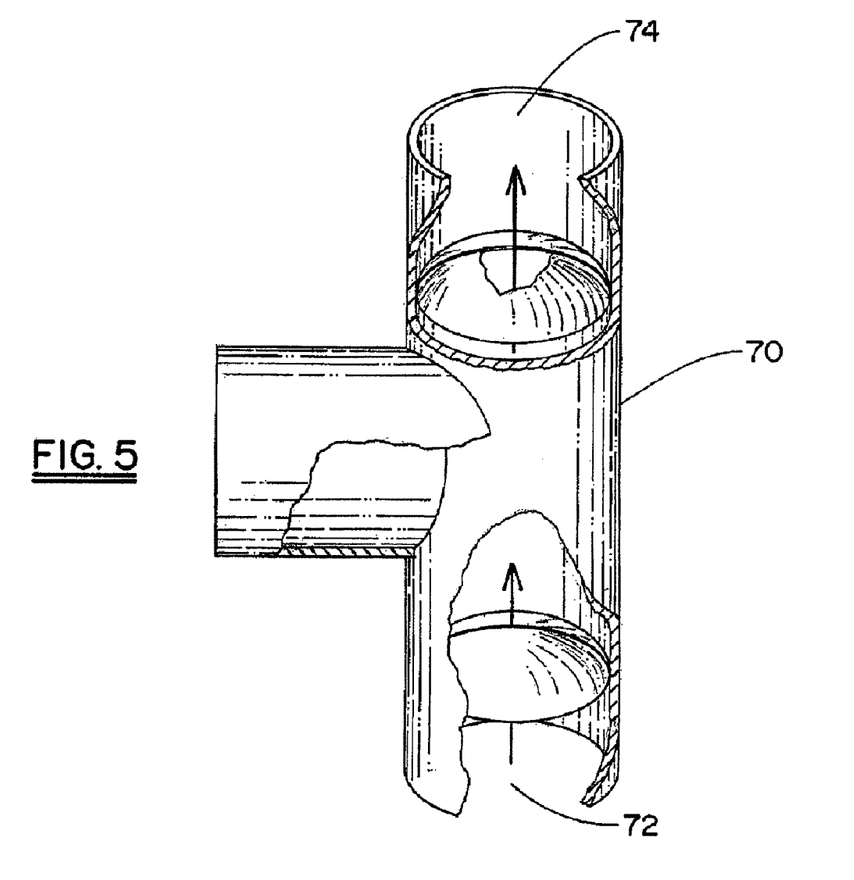
FIG. 5 is a perspective view of an attachment to the invention.

As seen in FIG. 5, a T-piece adaptor 70 may optionally be provided at open end 42 of breathing tube 34 for use with patients that are oxygen dependant. T-piece adapter 70 contains an inlet valve 72 and an outlet valve 74 which properly direct the passage of inhaled and exhaled air through the breathing tube 34. By connecting an oxygen dependant patient's supply to the intake valve 72, inhaled air can first be passed through the three sensors 36, 38, 40 to establish baseline readings of the oxygen and carbon dioxide concentrations for comparison to exhaled air, since an oxygen dependent patient receives air that has different concentrations than present in ambient air.

Data processing unit 50 comprises a commercially available computer processor programmed with software for the interpretation of the data obtained from measuring unit 30 and background comparison data. Software can be specifically developed to perform the necessary calculations to determine the partial pressures and carbon dioxide to oxygen ratios or software can optionally be purchased commercially and, if necessary, modified to run the appropriate algorithms. After additional research, the background comparison data can be updated based on data obtained from use of the invention to further refine expected normal values.

Display screen 60 comprises a cathode ray tube, plasma screen, or other visual display for displaying computerized data. Screen 60 can optionally display graphs representing predetermined reference or background data for test populations against which the current readings can be plotted for a visual comparison. In addition to displaying the carbon dioxide to oxygen ratios as a function of time calculated by data processing unit 50, screen 60 may optionally display a plot of the expired oxygen and carbon dioxide partial pressures. Using this display, a physician may estimate the efficiency of alveolar ventilation in patients with acute respiratory distress syndromes to assist in deciding the mechanical ventilation settings.

In addition to the three primary sensors 36, 38, 40, data processing unit 50 may optionally be connected to a pulse oximeter 44 that measures arterial oxygen saturation of hemoglobin in the arterial blood. From these data, and the additional measurement of pH and hemoglobin concentration in a peripheral venous blood sample, the cardiac output of the patient can be calculated according to the Fick equation. In order to perform the Fick equation, the average total oxygen consumed, the arterial oxygen content and venous oxygen content must be determined. The average total oxygen consumed can be determined from the oxygen tension and flow curves over a predetermined time period. For the purposes of determining cardiac output, a one minute time period is sufficient. The arterial oxygen content can be estimated by multiplying the arterial oxygen saturation (measured by pulse oximeter 44) by the hemoglobin concentration (determined from the venous blood sample). The venous oxygen content can be calculated by mathematical manipulation of the nadir (mean lowest) oxygen tension measured during deep expiration (in an awake patient) or a sign exhalation (in a mechanically ventilated patient) over the predetermined time period. From the nadir oxygen tension, venous oxygen saturation can be estimated according to published oxygen binding curves for the measured pH. The venous oxygen content is then calculated by multiplying the venous oxygen saturation by the venous hemoglobin (measured from the venous blood sample). Once these calculations have been made, the cardiac output is determined by dividing the total oxygen consumed by the difference between the arterial oxygen content and the venous oxygen content. The algorithm for the Fick calculation can be programmed into the data processing unit software and the results displayed on screen 60. The cardiac output measurement is useful for assisting the physician in determining the success or failure of treatment designed to relieve pulmonary vascular obstructions, or to treat circulatory shock.

Device 28 is used by having a patient breathe (inhale and exhale a predetermined number of times in succession) through mouthpiece 32 of the measuring unit 30. As the patient inhales and exhales the pneumotach flow sensor 36, capnometer 38, and oxygen monitor 40 perform their respective readings, which are then electrically transmitted via wires or cabling to data processing unit 50. The programmable software loaded into data processing unit 50 convert the measurements into volume and concentration readings, calculate the carbon dioxide to oxygen ratio, and display this ratio on screen 60 in the form of a graph against the volume of air expired. Readings may be optimized by requiring the patient to hold in inhaled air for several heartbeats before exhaling through the mouthpiece 32 of the measuring unit 30. It has been determined through testing that patients without a pulmonary embolism will normally have a carbon dioxide to oxygen ratio of 0.30 or greater while patients with a pulmonary embolism will have a carbon dioxide to oxygen ratio of 0.25 or less.

Figure 6:
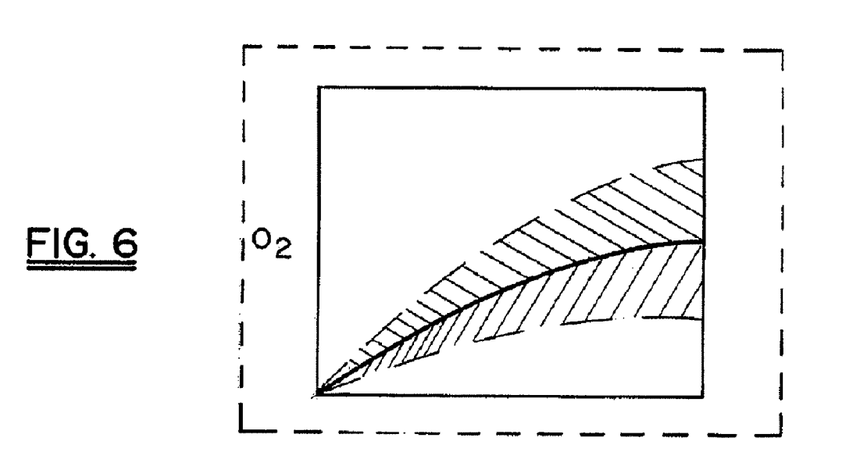
FIG. 6 is an illustration of a display screen readout.

Device 28 may also be used for the detection of whole-body oxygen consumption and determination of the adequacy of oxygen delivery during resuscitation from shock. During conditions of systemic inflammation the body will extract oxygen at higher levels than normal, resulting in an increase in the partial pressure of carbon dioxide-to-oxygen ratio in exhaled air. By using T-piece 70 in the manner explained above, the concentration of the oxygen provided to the patient and the concentration of the oxygen exhaled can be determined. As illustrated in FIG. 6, when the level of oxygen delivery (i.e., the amount provided minus the amount exhaled) observed at two inspired oxygen concentrations reaches normal levels a physician has visual conformation that the resuscitation performed is adequate. One method of determining the adequacy of resuscitation is to determine oxygen delivery at both relatively low fixed concentrations of oxygen and at relatively high fixed concentration. Relatively low concentrations include from about twenty-one to thirty percent (21-30%) oxygen and relatively high oxygen concentrations involve about forty-five to one hundred percent (45-100%) oxygen. The difference between oxygen delivery at relatively low concentrations verses relatively high concentrations can be compared against a nomogram for healthy patients of similar age, body mass, body mass index, and gender and used to assess the adequacy of fluid and vasopressor resuscitation.

Data processing unit 50 can additionally be programmed to display on screen 60 any of the individual measurements taken by sensors 36, 38, 40, and 44, or combinations thereof for diagnostic purposes. For example, a plot of the expired carbon dioxide and oxygen concentration over time could be used to estimate the efficiency of alveolar ventilation in patients with acute respiratory distress syndrome. Additionally, the plotted data from sensors 36, 38, 40, and 44 could be used to assist in deciding how to properly adjust mechanical ventilators setting, such as the degree of positive end-expiratory pressure, minute ventilation, and peak inspiratory pressure settings, to optimize patient care. For example, data from sensors 36, 37, 40, and 44, can be plotted individually in patients who are being mechanically ventilated. By simultaneously plotting the partial pressures of oxygen and carbon dioxide as a function of volume of each breath, the amount of carbon dioxide released and percentage of oxygen extracted can be determined. If the barometric pressure is known or inputted into data processing unit 50, the efficiency of alveolar ventilation during each tidal volume breath can be calculated. This information can then be used to adjust mechanical ventilation to optimize alveolar efficiency or breathing alveolar ventilation efficiency.

The device of the present invention allows for testing at the bedside and can be used to monitor for pulmonary embolism perioperatively. The device of the present invention may be used to take a baseline set of breath measurements of a patient at moderate- to high-risk for pulmonary embolism, the data may be stored, and then the baseline may for comparison to patient data obtained in the post operative phase. It will be obvious to anyone skilled in the art that this method can be used to monitor patients exposed to other recognized risks of pulmonary embolism, including deep venous thrombosis, heart failure, pregnancy, cancer, skeletal fractures, immobility, paralysis, drug therapy.

Figure 7:
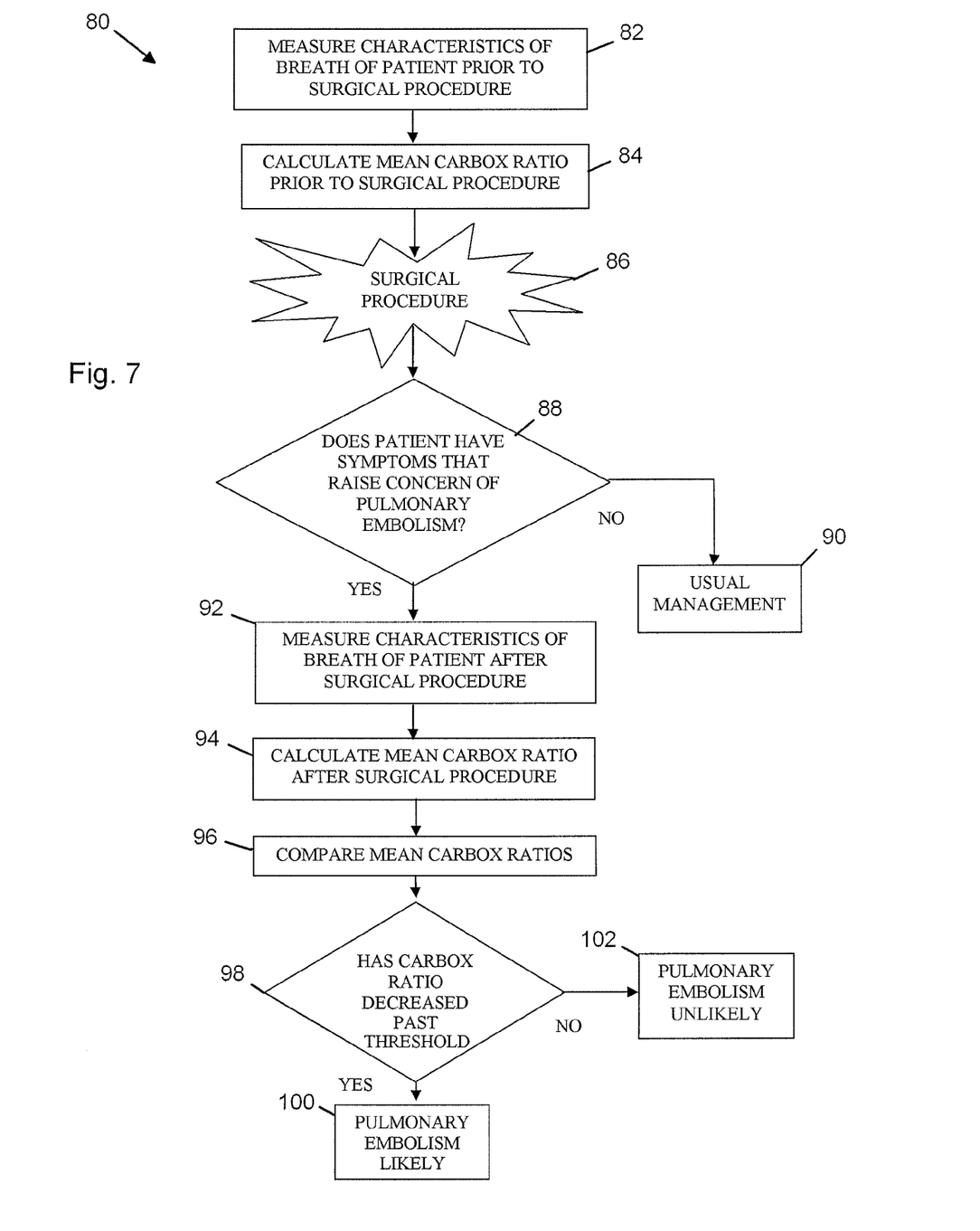
FIG. 7 is a flowchart of a method of non-invasively indicating the presence of pulmonary embolism in a post-operative patient.

Referring to FIG. 7, the first step in the intraoperative process 80 is to take baseline measurements 82 during preoperative screening. Prior to obtaining the data, data processing unit 50 should be provided with patient anthropomorphic, identifying and demographic data. The data may be inputted manually, or retrieved from a patient electronic records database. The requisite measurements to be taken for the baseline include the tidal volume, respiratory rate, minute ventilation, peak inspiratory and expiratory flows, airstream temperature, expired partial pressures of $CO_2$ and $O_2$, and an automated secondary computation of the estimated airway deadspace using the method of Fletcher. The key respiratory-derived variable of interest is the "carbox ratio," which is the instantaneous ratio of expired partial pressure of carbon dioxide (pCO2) divided by the partial pressure of oxygen (pO2) at or near the end of a tidal volume breath. As explained above, the device of the present invention also records flow and volume, and allows computation of many variables derived from these measurements.

During the collection stage, the patient is allowed to breathe the ambient air for two minutes, and is then seated in a semi-Fowler's position and given with comfortable nose clips. The patient is then provided with and breathes through mouthpiece 32 of the device of the present invention. Data processing unit 50 evaluates each breath against preset criteria for suitability. For example, data processing unit 50 may be programmed to accept a minimum of 5 and a maximum of 10 breaths that satisfy predetermined criteria for suitability, such as the requirement that each breath need have an acceptable tidal volume as predicted from nomograms for height, age, gender, and race. When an adequate number of breaths that meet the criteria are obtained, the nose clips removed and data collection 82 is complete. From the data collected, the mean carbox ratio prior to a surgical procedure may be calculated 84. The data obtained during this stage, including the carbox ratio, may be stored in a nonvolatile memory for comparison to subsequently obtained data.

After a surgical procedure 86, a check is performed 88 to see whether the patient is having any difficult breathing. If not, the usual management of the patient is performed. If so, the data collection stage describe above is repeated to measure the characteristics of the breath of the patient after the surgical procedure 92. Data processing unit 50 then calculates the mean carbox ratio after the procedure 94, and compares it to the mean baseline carbox ratio 96 from baseline collection 82 and calculation 84.

A check 98 is then performed to see whether the carbox ratio has decreased past a predetermined threshold that signals the possibility of pulmonary embolism. For example, a threshold decrease in the carbox ratio of more than about twenty-five percent (25%) may represent an abnormal condition that is consistent with possible pulmonary embolism 100. No change or an increase in the carbox ratio suggests that pulmonary embolism is unlikely 102. Similar logic can be used to compare other breathing parameters, including tidal volume, minute ventilation, airway deadspace, flow rates and various arithmetic manipulations of these variables to the baseline measurement to indicate other possible sources for the breathing difficulty. For example, measurements of airway restriction as the possible cause of respiratory symptoms include measurement of flow-volume loops, FEV1, FVC, and the slope of the alveolar plateau observed on a real-time plot of the carbox ratio.

Figure 8A:
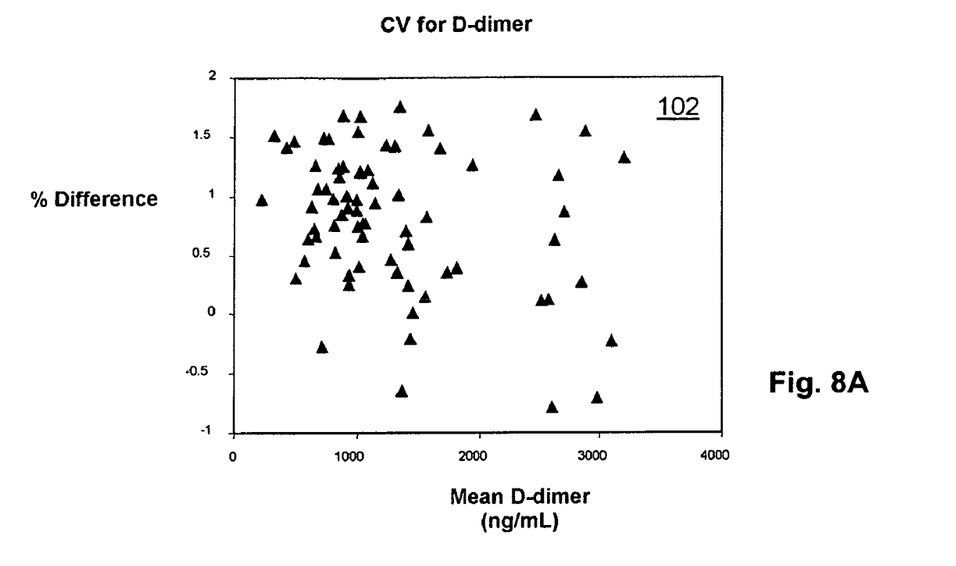
FIGS. 8A and B are scatter plots showing the accuracy of the present invention as compared to a convention method of determining the presence of pulmonary embolism.
Figure 8B:
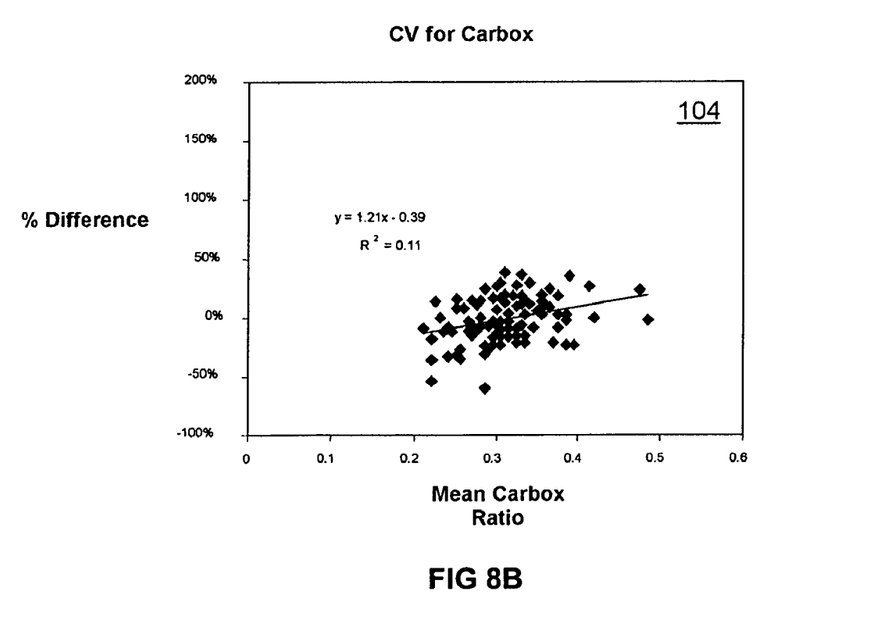

As seen in FIGS. 8A and B, statistical analysis 102 of the D-dimer test reveals that the test is very unpredictable when used postoperatively. In particular, the D-dimer suffers from very low diagnostic specificity in the post-surgical population. By comparison, statistical analysis 104 of intraoperative process 80 according to the present invention provides potential for higher diagnostic specificity. The mean coefficient of variability for the D-dimer when measured preoperatively then on schedule two to three days postoperatively is 65 percent. The coefficient of variability of intraoperative process 80, however, is only 16 percent. Thus, intraoperative process 80 is a more stable measurement in patients at high risk for pulmonary embolism who did not previously have pulmonary embolism.

What is claimed is:

1. A method of determining a likelihood of a pulmonary embolism in a patient, comprising the steps of:
   determining the carbox ratio of said patient prior to a surgical procedure;
   determining the carbox ratio of said patient after to the surgical procedure;
   comparing said carbox ratio of said patient prior to the surgical procedure to said carbox ratio of said patient after the surgical procedure using a processing device; and
   determining the likelihood of a pulmonary embolism in said patient based on said comparing step.

2. The method of claim 1, wherein the step of determining the carbox ratio of said patient prior to a surgical procedure comprises the step of measuring the instantaneous ratio of expired partial pressure of carbon dioxide divided by the partial pressure of oxygen (pO2) at or near the end of a predetermined number of tidal volume breaths.

3. The method of claim 2, wherein the step of determining the carbox ratio of said patient after to a surgical procedure comprises the step of measuring the instantaneous ratio of expired partial pressure of carbon dioxide divided by the partial pressure of oxygen (pO2) at or near the end of a predetermined number of tidal volume breaths.

4. The method of claim 3, wherein a pulmonary embolism is likely present in said patient when said carbox ratio of said patient after to the surgical procedure is twenty-five or more percent less than said carbox ratio of said patient prior to the surgical procedure.

5. The method of claim 3, wherein a pulmonary embolism is likely not present in said patient when said carbox ratio of said patient after to the surgical procedure is equal to or more than said carbox ratio of said patient prior to the surgical procedure.

6. The method of claim 3, wherein the step of determining the carbox ratio of said patient after to the surgical procedure is performed if the patient has difficulty breathing.

7. The method of claim 1, wherein said carbox ratio of said patient prior to a surgical procedure and said carbox ratio of said patient after to a surgical procedure are stored in non-volatile memory.

8. A method of determining a likelihood of a pulmonary embolism in a patient, comprising the steps of:
measuring characteristics of the breath of the patient prior to a surgical procedure;
measuring characteristics of the breath of the patient after the surgical procedure;
comparing the characteristics of the breath of the patient prior to the surgical procedure with the characteristics of the breath of the patient after the surgical procedure using a processing device; and
determining the likelihood of a pulmonary embolism in said patient based on said comparing step.

9. The method of claim 8, wherein said characteristics of the breath of the patient comprise one or more characteristics selected from the group consisting of tidal volume, respiratory rate, minute ventilation, peak inspiratory flow, peak expiratory flow, expired partial pressures of CO2, and expired partial pressures of O2.

10. The method of claim 9, wherein the carbox ratio of the patient prior to the surgical procedure is calculated from characteristics of the breath of the patient prior to the surgical procedure.

11. The method of claim 10, wherein the carbox ratio of the patient after the surgical procedure is calculated from characteristics of the breath of the patient after to the surgical procedure.

12. The method of claim 11, wherein the step of comparing the characteristics of the breath of the patient prior to the surgical procedure with the characteristics of the breath of the patient after the surgical procedure comprises comparing the carbox ratio of the patient prior to the surgical procedure to the carbox ratio of the patient after the surgical procedure.

13. The method of claim 12, wherein the step of measuring characteristics of the breath of the patient prior to the surgical procedure is performed while the patient is seated in the semi-Fowler's position.

14. The method of claim 13, wherein the step of measuring characteristics of the breath of the patient prior to the surgical procedure is performed after the patient breathes ambient air for at least two minutes.

15. The method of claim 12, wherein the step of measuring characteristics of the breath of the patient prior to a surgical procedure is performed while the patient is wearing nose clips.

16. The method of claim 13, wherein the step of measuring characteristics of the breath of the patient after the surgical procedure is performed after the patient breathes ambient air for at least two minutes.

17. A method of determining a likelihood of a pulmonary embolism in a surgical patient, comprising the steps of:
(a) allowing the patient to breathe ambient air for at least two minutes prior to a surgical procedure;
(b) seating the patient in the semi-Fowler's position prior to the surgical procedure;
(c) placing nose clips on the patient prior to the surgical procedure;
(d) measuring characteristics of the breath of the patient prior to the surgical procedure;
(e) storing the characteristics of the breath of the patient in non-volatile memory prior to the surgical procedure;
(f) repeating steps (a) through (d) after the surgical procedure;
(g) calculating the carbox ratio of the patient from the characteristics of the breath of the patient prior to the surgical procedure;
(h) calculating the carbox ratio of the patient from the characteristics of the breath of the patient after the surgical procedure; and
(i) comparing characteristics of the breath of the patient prior to the surgical procedure with the characteristics of the breath of the patient prior to the surgical procedure using a processing device; and
(j) determining the likelihood of a pulmonary embolism in said patient based on said comparing step.

18. The method of claim 17, wherein the characteristics of the breath of the patient comprise one or more parameters selected from the group consisting of tidal volume, respiratory rate, minute ventilation, peak inspiratory flow, peak expiratory flow, expired partial pressures of CO2, and expired partial pressures of O2.

19. The method of claim 18, wherein a pulmonary embolism is likely present in said patient when said carbox ratio of said patient after to the surgical procedure is twenty-five or more percent less than said carbox ratio of said patient prior to the surgical procedure.

20. The method of claim 18, wherein a pulmonary embolism is likely not present in said patient when said carbox ratio of said patient after to the surgical procedure is equal to or more than said carbox ratio of said patient prior to the surgical procedure.

\* \* \* \* \*